United States Patent
Yu et al.

(10) Patent No.: US 8,431,001 B2
(45) Date of Patent: Apr. 30, 2013

(54) ION SENSOR FOR MEASURING ION CONCENTRATION OF A SOLUTION

(75) Inventors: Peichen Yu, Hsinchu (TW); Bing-Mau Chen, Hsinchu County (TW); Chia-Hua Chang, New Taipei (TW); Min-Hsiang Hsu, New Taipei (TW); Chan-Hung Huang, Hsinchu County (TW); Chen-Hao Kuo, Kaohsiung (TW)

(73) Assignee: National Chiao Tung University, Hsinchu (TW)

( * ) Notice: Subject to any disclaimer, the term of this patent is extended or adjusted under 35 U.S.C. 154(b) by 76 days.

(21) Appl. No.: 13/041,167

(22) Filed: Mar. 4, 2011

(65) Prior Publication Data

US 2012/0048733 A1 Mar. 1, 2012

(30) Foreign Application Priority Data

Sep. 1, 2010 (TW) .............................. 99129471 A

(51) Int. Cl.
*G01N 27/333* (2006.01)
(52) U.S. Cl.
USPC ............................ 204/416; 204/400; 257/253
(58) Field of Classification Search .................. 257/253; 204/400, 416–418
See application file for complete search history.

(56) References Cited

U.S. PATENT DOCUMENTS

| | | | | |
|---|---|---|---|---|
| 4,180,771 A | 12/1979 | Guckel | | 324/71 |
| 4,446,474 A | 5/1984 | Mizusaki | | 357/25 |
| 6,464,940 B1 | 10/2002 | Akioka | | 422/82 |
| 2006/0220092 A1 | 10/2006 | Chou | | 257/411 |
| 2007/0001253 A1 | 1/2007 | Hsiung | | 257/192 |
| 2008/0277746 A1 | 11/2008 | Hsu | | 257/414 |
| 2009/0145755 A1* | 6/2009 | Edelbrock | | 204/403.14 |
| 2009/0278175 A1* | 11/2009 | Chou et al. | | 257/253 |
| 2010/0040859 A1 | 2/2010 | Chang | | 427/596 |

OTHER PUBLICATIONS

Liao et al., Materials Chemistry and Physics 114:542-548.*
Zhao et al., Electrochim. Acta 55:5647-5651.*
Asif et al., Appl. Phys. Lett. 95:123703.*
Greene et al. Angew. Chem. Int. Ed., 42:3031-3034.*
Antohe et al., Appl. Phys. Lett. 94:073118.*

* cited by examiner

*Primary Examiner* — Luan Van
*Assistant Examiner* — Steven Rosenwald
(74) *Attorney, Agent, or Firm* — Ladas & Parry, LLP

(57) ABSTRACT

An ion sensor includes: a conductive base structure including a substrate and an electrode film formed on the substrate; a plurality of ion-sensitive nanorods protruding from the electrode film; and an encapsulant enclosing the conductive base structure, surrounding the ion-sensitive nanorods, and formed with a window for exposing the ion-sensitive nanorods. Each of the ion-sensitive nanorods has a conductive core and an ion-sensitive layer formed on and enclosing the conductive core. The ion-sensitive material exhibits an ion selectivity of absorbing an ion of interest thereon for inducing a surface potential corresponding to concentration of the ion of interest.

18 Claims, 4 Drawing Sheets

ION SENSOR FOR MEASURING ION CONCENTRATION OF A SOLUTION

CROSS-REFERENCE TO RELATED APPLICATIONS

This application claims priority of Taiwanese Patent Application No. 099129471 filed on Sep. 1, 2010, the disclosures of which is incorporated herein by reference.

BACKGROUND OF THE INVENTION

1. Field of the Invention

The invention relates to an ion sensor for measuring ion concentration of a solution, more particularly to an ion sensor including a plurality of ion-sensitive nanorods protruding from a conductive base structure.

2. Description of the Related Art

Ion sensors are useful for measuring concentration of an ion of interest in a solution, and can selectively absorb the ions on a surface thereof, which induces a surface potential thereat due to the total charge of the absorbed ions. Hence, by measuring the surface potential of the ion sensor, the ion concentration of the solution can be determined.

U.S. Pat. No. 4,180,771 discloses a chemical sensitive field effect transistor that includes a semiconductor substrate having a source region and a drain region, a gate dielectric film formed on a top side of the semiconductor substrate, three electrodes formed on the source region, the drain region and the gate dielectric film, respectively, a chemical sensitive film formed on a bottom side of the semiconductor substrate, and a reference electrode formed on the chemical sensitive film. In use, when the chemical sensitive film is brought into contact with a solution for measuring ion concentration of the solution, a surface potential of the chemical sensitive film is changed, which, changes the electric field in the semiconductor substrate, which, in turn, changes the conductivity of a channel region of the semiconductor substrate between the source region and the drain region. Hence, by measuring the current passing through the source region and the drain region of the semiconductor substrate, the ion concentration can be determined.

U.S. Pat. No. 4,446,474 discloses an ion sensitive field effect transistor (ISFET) that includes a semiconductor substrate having a source region and a drain region, a gate dielectric film formed on the semiconductor substrate, an inorganic insulator protecting film formed on the gate dielectric film, and a sensitive film formed on the inorganic insulator protecting film and capable of absorbing selectively ions to generate a surface potential for measuring ion concentration.

U.S. Patent Application Publication No. 2006/0220092 discloses an extended gate field effect transistor (EGFET) ion sensor that includes a semiconductor silicon substrate, a titanium dioxide sensitive film formed on the semiconductor silicon substrate, and a metal-oxide-semiconductor-field-effect transistor (MOSFET) connected electrically to the titanium dioxide sensitive film through a conductive wire. In use, only the assembly of the semiconductor silicon substrate and the titanium dioxide sensitive film is needed to be immersed in the solution for measuring ion concentration of the solution through a buildup surface potential at the surface of the titanium dioxide sensitive film.

U.S. Patent Application Publication No. 2007/0001253 discloses an extended gate field effect transistor (EGFET) ion sensor that includes an ion sensitive component and a MOSFET connected electrically to the ion sensitive component. The ion sensitive component includes a glass substrate, an indium tin oxide (ITO) film formed on the glass substrate, a tin oxide sensitive film formed on the ITO film, and an enzyme chemical film formed on the tin oxide sensitive film.

U.S. Pat. No. 6,464,940 discloses a pH sensor that includes a semiconductor substrate (n-type silicon substrate with an n-channel), a silicon dioxide sensitive film formed on a top side of the semiconductor substrate, a liquid storing part formed on the silicon dioxide sensitive film, a first electrode formed on the liquid storing part, and a second electrode formed on a bottom side of the semiconductor substrate. When a solution to be analyzed is fed into the liquid storing part to contact the silicon dioxide sensitive film, a surface potential at a contact surface of the silicon dioxide sensitive film is produced and the capacitance of the n-channel is changed. Hence, by measuring the capacitance and the voltage of the pH sensor, ion concentration of the solution can be determined.

U.S. Patent application Publication No. 2008/0277746 discloses a nanowire sensor with self-aligned electrode support. The nanowire sensor includes a doped silicon-containing substrate, a growth-promoting metal layer formed on the silicon-containing substrate, a silicon nitride support formed on the growth-promoting metal layer, a plurality of nanowires formed on the growth-promoting metal layer, and a top electrode formed on top ends of the nanowires. The top electrode also plays a role of protecting the nanowires from damage. It is noted that since the top electrode is formed on the top ends of the nanowires, the nanowire sensor can only be used for detecting gases. If the nanowire sensor is to be used for detecting ions in a solution, the potential of the top electrode tends to be interfered by the ions in the solution, which can cause the function of the nanowires to fail.

The whole disclosures of the aforesaid patents are incorporated herein by reference.

SUMMARY OF THE INVENTION

The object of the present invention is to provide an ion sensor including a plurality of ion-sensitive nanorods so as to enlarge a contact surface of the ion sensor for measuring ion concentration of a solution.

According to the present invention, there is provided an ion sensor for measuring ion concentration of a solution. The ion sensor comprises: a conductive base structure including a substrate and an electrode film formed on the substrate and having a sensing region; a plurality of ion-sensitive nanorods protruding from one side of the electrode film opposite to the substrate, covering entirely the sensing region of the electrode film, and exhibiting an ion selectivity of absorbing an ion of interest thereon for inducing a surface potential corresponding to concentration of the ion of interest in the solution; and an encapsulant of an insulator enclosing the conductive base structure except for the sensing region of the electrode film and formed with a window for exposing the ion-sensitive nanorods to the solution.

BRIEF DESCRIPTION OF THE DRAWINGS

In drawings which illustrate an embodiment of the invention.

DETAILED DESCRIPTION OF THE PREFERRED EMBODIMENT

Figure 1:
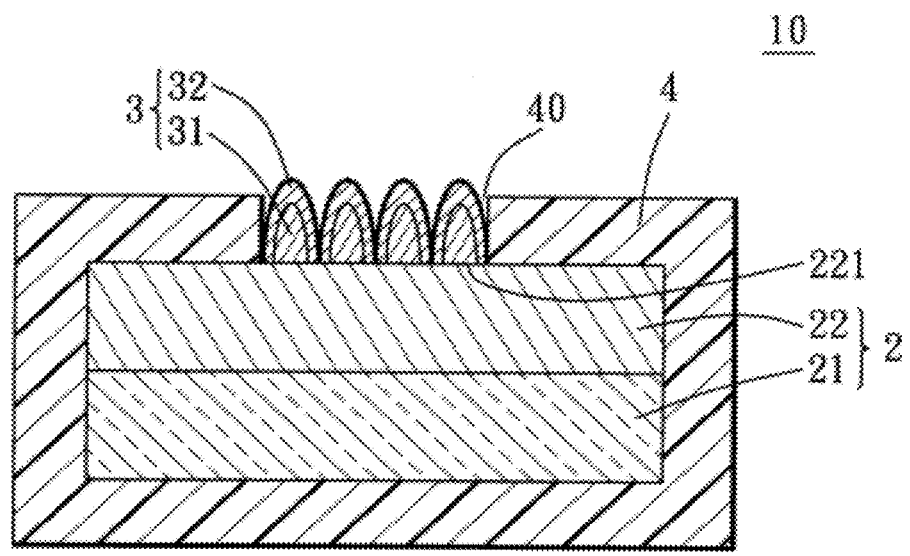
FIG. 1 is a schematic sectional view of the preferred embodiment of an ion sensor according to this invention.
Figure 2:
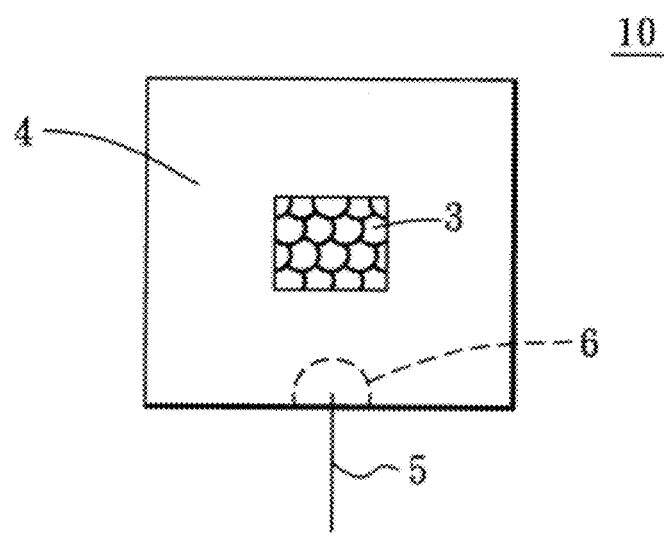
FIG. 2 is a schematic top view of the preferred embodiment.

Referring to FIGS. 1 and 2, the ion sensor 10 of the preferred embodiment of the present invention for measuring ion concentration of a solution 12 in a container of an ion concentration measuring system (see FIG. 5) includes: a conductive base structure 2 including a substrate 21 and an electrode film 22 formed on the substrate 21 and having a sensing region 221; a plurality of ion-sensitive nanorods 3 protruding from one side of the electrode film 22 opposite to the substrate 21 and covering entirely the sensing region 221 of the electrode film 22; a conductive line 5 having one end attached securely to the electrode film 22 through a conductive paste 6; and an encapsulant 4 of an insulator enclosing the conductive base structure 2 except for the sensing region 221 of the electrode film 22, covering the end of the conductive line 5 and the conductive paste 6, surrounding the ion-sensitive nanorods 3, and formed with a window 40 for exposing the ion-sensitive nanorods 3 to the solution 12. Each of the ion-sensitive nanorods 3 has a conductive core 31 made from an electrically conductive material and protruding from the electrode film 22, and an ion-sensitive layer 32 formed on and enclosing the conductive core 31 and made from an ion-sensitive material different from the electrically conductive material. The ion-sensitive material exhibits an ion selectivity of absorbing an ion of interest thereon for inducing a surface potential corresponding to concentration of the ion of interest in the solution 12. The conductive line 5 can be connected to a differential amplifier 13 (see FIG. 5) or a metal-oxide-semiconductor-field-effect transistor (MOSFET) (not shown) for measuring an output voltage of the ion sensor 10 corresponding to the ion concentration of the solution 12.

The substrate 21 may be made from a rigid and non-corrosive material, such as glass. Preferably, the electrode film 22 is made from the electrically conductive material.

The electrically conductive material is preferably indium tin oxide (ITO), tin oxide, or indium oxide, and more preferably ITO. A conventional ITO glass substrate includes a glass substrate and an indium tin oxide film coated on the glass substrate, and is a suitable candidate for serving as the conductive base structure 2.

The ion-sensitive material is preferably titanium dioxide, tin dioxide, zinc oxide, ruthenium oxide, or iridium oxide, and more preferably titanium dioxide.

Suitable material of the insulator of the encapsulant 4 may be made from a curable resin, such as epoxy resin.

In the preferred embodiment, the conductive line 5 is a conductive wire and the conductive paste 6 is a silver paste.

Preferably, the conductive core 31 of each of the ion-sensitive nanorods 3 has a diameter ranging from 10-50 nm. Preferably, the ion-sensitive layer 32 of each of the ion-sensitive nanorods 3 has a layer thickness ranging from 10-120 nm.

Formation of the conductive cores 31 on the electrode film 22 can be carried out by the method disclosed in U.S. Patent Application Publication No. 2010/0040859, the whole disclosure of which is incorporated herein by reference. The method involves the use of an electron beam system to evaporate a target source controlled in an oblique-angle deposition manner. Suitable operating conditions for forming the conductive cores 31 on the electrode film 22 using the aforesaid method are as follows. The temperature in a sputtering chamber (not shown) for forming the conductive cores 31 preferably ranges from 100-450° C., the flow rate of nitrogen introduced into the sputtering chamber is preferably greater than zero sccm and less than 50 sccm, a flow rate of oxygen introduced into the sputtering chamber is preferably greater than zero scorn and less than 50 sccm, the vacuum pressure of the sputtering chamber is controlled at about $10^{-3}$-$10^{-6}$ torr, and the angle between the incident direction of particles evaporated from a target source and the normal direction of an evaporation substrate where the target source is placed (detailed illustration of the angle is referred to the disclosure of U.S. Patent Application Publication No. 2010/0040859) is preferably greater than zero degree and less than 90 degrees.

The following Example and Comparative Example are provided to illustrate the merits of the preferred embodiment of the invention, and should not be construed as limiting the scope of the invention.

Example 1

Preparation of the Conductive Cores

Figure 3:
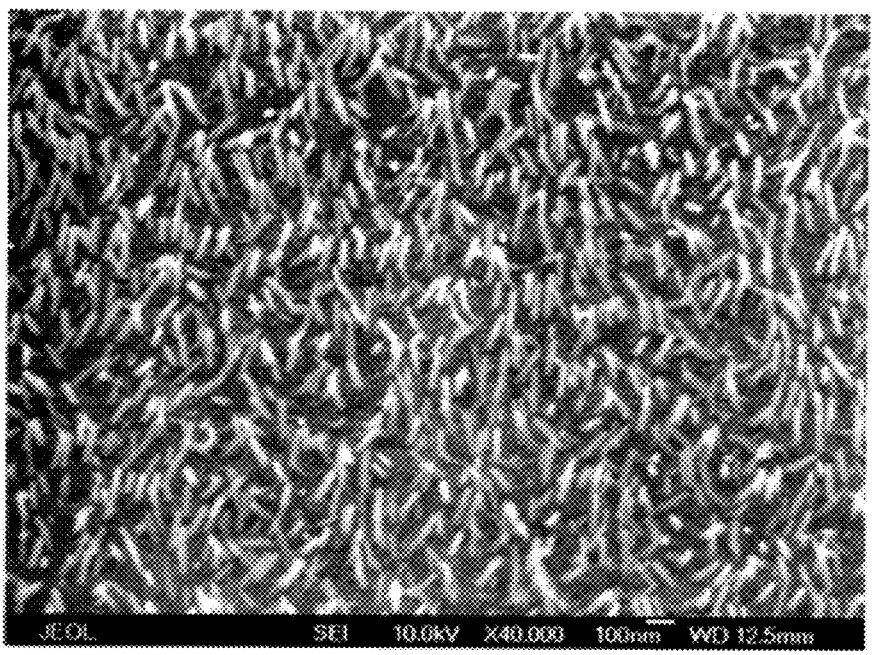
FIG. 3 is a SEM photo showing the structure of a plurality of conductive cores protruding from an electrode film of the preferred embodiment.

The conductive cores 31 were formed on an ITO glass substrate by using an electron beam system disclosed in the aforesaid U.S. Patent Application Publication No. 2010/0040859. The operating conditions of forming the conductive cores 31 were as follows: the temperature of the sputtering chamber was controlled at about 260° C., the flow rate of nitrogen was about 1 sccm, the flow rate of oxygen was about 1 sccm, the vacuum pressure of the sputtering chamber was controlled at a range of from $1\times10^{-4}$ torr to $3\times10^{-4}$ torr, and the angle between the incident direction of particles and the normal direction of the evaporation substrate was about 70 degrees. The conductive cores 31 thus formed have a length ranging from 80 to 120 nm and a diameter ranging from 10 to 50 nm. FIG. 3 is a SEM photo of the conductive cores 31 thus formed.

Preparation of the Ion-Sensitive Nanorods

Figure 4:
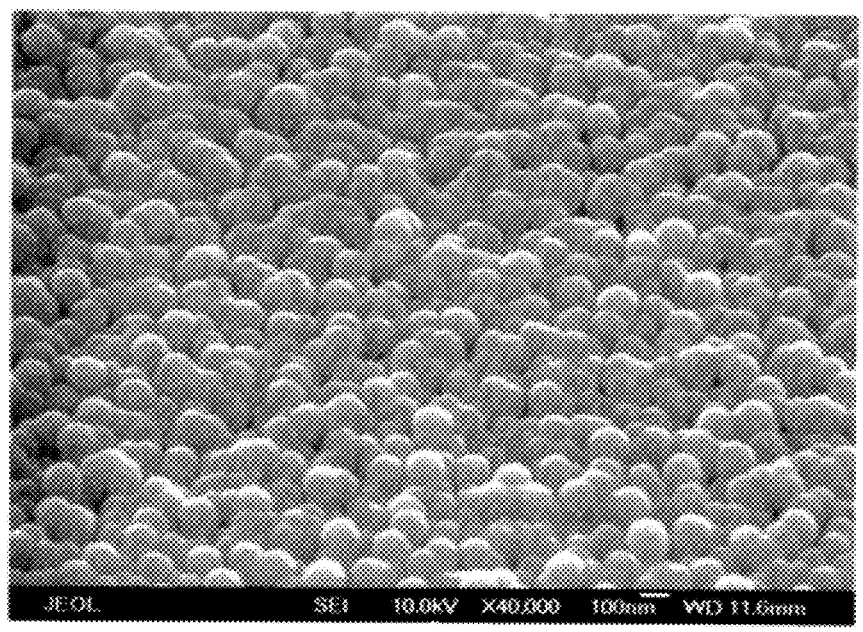
FIG. 4 is a SEM photo showing the structure of a plurality of ion-sensitive nanorods protruding from the electrode film of the preferred embodiment.

The conductive cores 31 together with the ITO glass substrate were vapor deposited with a titanium dioxide layer (serving as the ion-sensitive layer 32) using vacuum sputtering techniques. The operating conditions for forming the titanium dioxide layer are as follows: a flow rate ratio of $Ar/O_2$ was controlled at about 3/1, a RF power of 150 W was employed for sputtering a target source, the temperature of the sputtering chamber was controlled at about 35° C., and the vacuum pressure of the sputtering chamber was controlled at about $1\times10^{-6}$ torr. The ion-sensitive layers 32 of the ion-sensitive nanorods 3 thus formed have a layer thickness ranging from 10 to 90 nm. FIG. 4 is a SEM photo of the ion-sensitive nanorods 3 thus formed.

Encapsulation to Form the Ion Sensor

A masking tape (not shown) was used to cover the ion-sensitive nanorods 3, followed by fixing one end of a conductive wire (serving as the conductive line 5) to the ITO glass substrate through a silver paste 6, enclosing the ITO glass substrate except for the masking tape using an epoxy resin, and removing the masking tape after the encapsulation so as to expose the ion-sensitive nanorods 3.

Comparative Example

The ion sensor of Comparative Example was formed by depositing a titanium dioxide film on the ITO substrate (no conductive cores were formed on the ITO substrate) through the sputtering techniques with operating conditions similar to those of Example 1. The titanium dioxide film thus formed has a layer thickness of about 90 nm.

Performance Test

Figure 5:
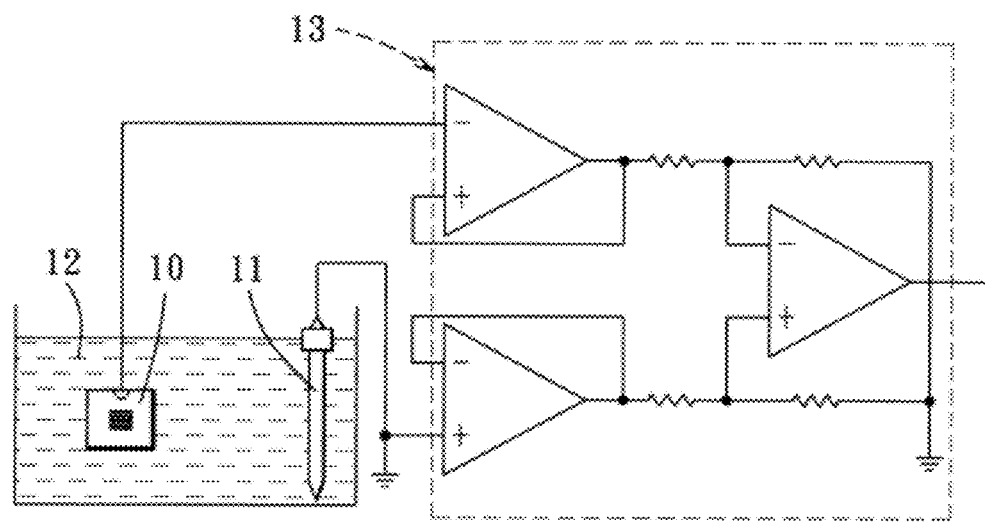
FIG. 5 is a schematic view showing how the preferred embodiment is used in an ion concentration measuring system.

Performance tests for the ion sensors of Example 1 and Comparative Example were carried out by using the ion concentration measuring system (see FIG. 5). The ion sensor 10 to be tested and a reference electrode 11 were immersed in the solution 12 and were connected to a voltage meter (not shown) through the differential amplifier 13. In the performance test, an output voltage of the ion sensor 10 corresponding to the pH value of the solution 12 was measured by the voltage meter. Measurements of the output voltage for different solutions 12 having different ion concentrations (different pH values) were repeated.

Figure 6:
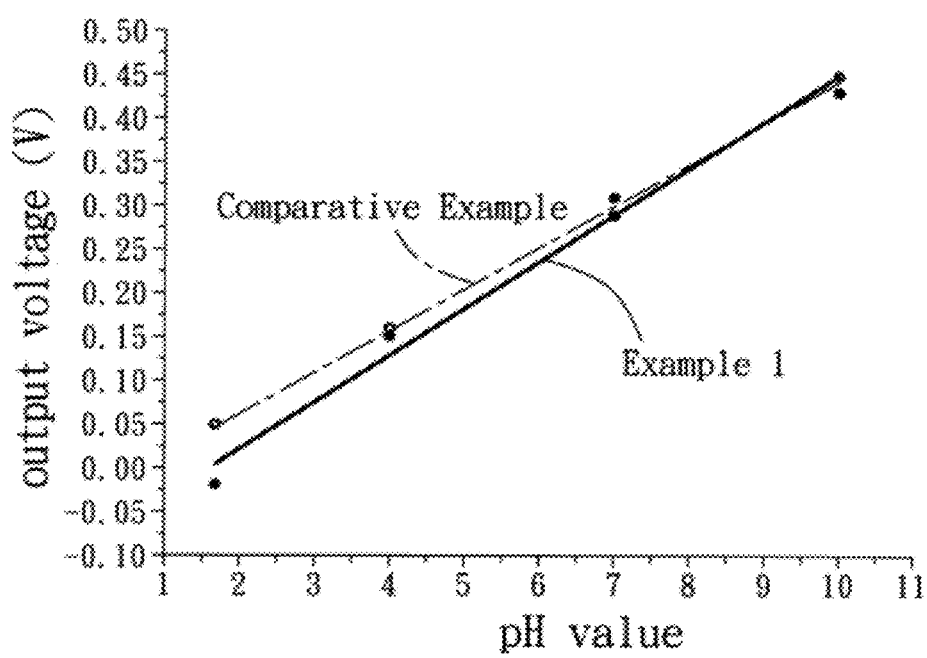
FIG. 6 is a plot of output voltage vs. pH value for Example 1 and Comparative Example 1.

FIG. 6 shows the relation between the output voltage and the pH value for the performance tests of Example 1 and Comparative Example. Based on the results shown in FIG. 6, the sensitivities and linearities of the ion sensors of Example 1 and Comparative Example can be calculated. The sensitivity and linearity of the ion sensor of Example 1 are 53.4 mV/pH and 0.976, respectively, while the sensitivity and linearity of the ion sensor of Comparative Example are 47.4 mV/pH and 0.997, respectively.

Figure 7:
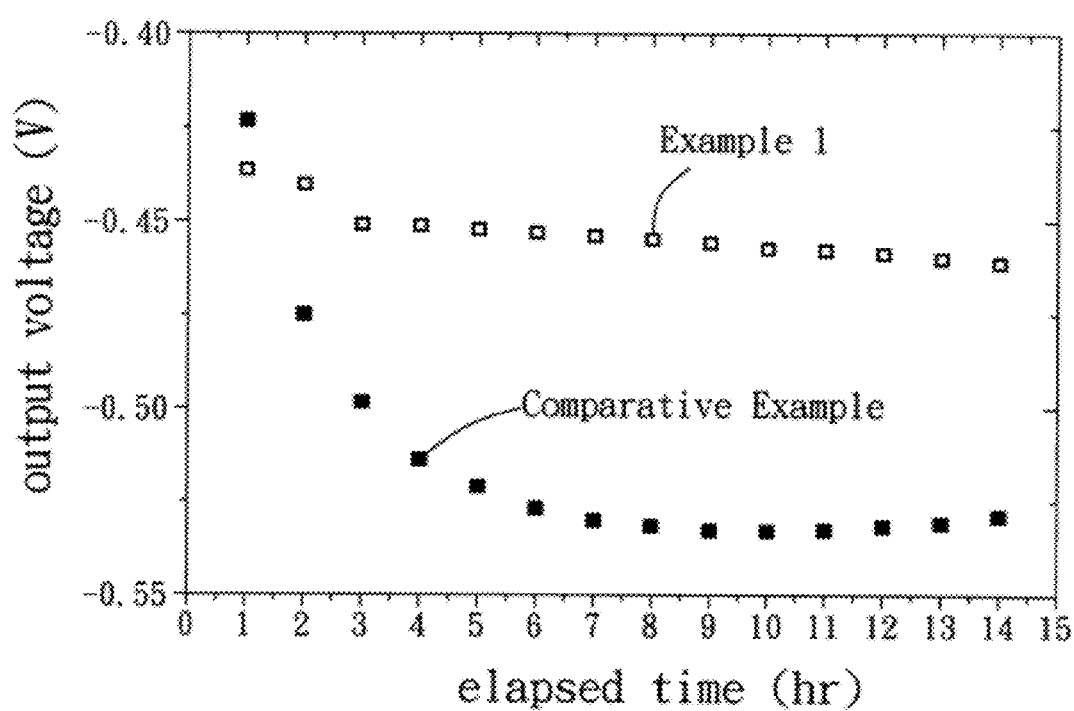
FIG. 7 is a plot of output voltage vs. elapsed time for Example 1 and Comparative Example 1.

FIG. 7 shows the relation between the output voltage and the elapsed time for the performance tests of Example 1 and Comparative Example, with the pH of the solution being maintained at 10. Based on the results of FIG. 7, a voltage drift (unit: mV/hr) of the ion sensor of each of Example 1 and Comparative Example can be calculated. The results show that the ion sensor of Example 1 has a voltage drift of about 2.26 mV/hr during the elapsed time from the beginning to 7 hrs and a voltage drift of about 1.0 mV/hr after 7 hrs of the elapsed time, and that the ion sensor of Comparative Example has a voltage drift of about 15.2 mV/hr during the elapsed time from the beginning to 7 hrs and a voltage drift of about 1.28 mV/hr after 7 hrs of the elapsed time.

By forming the ion-sensitive nanorods 3 on the conductive base structure 2 of the ion sensor of this invention, the sensitivity and the voltage drift of the ion sensor of this invention can be improved as compared to the conventional ion sensor.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. An ion sensor for measuring ion concentration of a solution, comprising:
    a conductive base structure including a substrate and an electrode film formed on said substrate and having a sensing region;
    a plurality of ion-sensitive nanorods protruding from one side of said electrode film opposite to said substrate, covering entirely said sensing region of said electrode film, and exhibiting an ion selectivity of absorbing an ion of interest thereon for inducing a surface potential corresponding to concentration of the ion of interest in the solution; and
    an encapsulant of an insulator enclosing said conductive base structure except for said sensing region of said electrode film and formed with a window for exposing said ion-sensitive nanorods to the solution,
    wherein each of said ion-sensitive nanorods has a conductive core made from an electrically conductive material and protruding from said electrode film, and an ion-sensitive layer formed on and enclosing said conductive core and made from an ion-sensitive material different from said electrically conductive material, said ion-sensitive material exhibiting the ion selectivity, and
    wherein said electrically conductive material is indium tin oxide, tin oxide, or indium oxide.

2. The ion sensor of claim 1, wherein said conductive core of each of said ion-sensitive nanorods has a diameter ranging from 10-50 nm.

3. The ion sensor of claim 1, wherein said ion-sensitive layer of each of said ion-sensitive nanorods has a layer thickness ranging from 10-90 nm.

4. The ion sensor of claim 1, wherein said electrode film is made from said electrically conductive material.

5. The ion sensor of claim 1, wherein said electrically conductive material is indium tin oxide.

6. The ion sensor of claim 1, wherein said ion-sensitive material is selected from titanium dioxide, tin dioxide, zinc oxide, ruthenium oxide, and iridium oxide.

7. The ion sensor of claim 6, wherein said ion-sensitive material is titanium dioxide.

8. The ion sensor of claim 1, wherein said insulator of said encapsulant is made from epoxy resin.

9. The ion sensor of claim 1, wherein said substrate is made from glass.

10. An ion sensor for measuring ion concentration of a solution, comprising:
    a conductive base structure including a substrate and an electrode film formed on said substrate and having a sensing region;
    a plurality of ion-sensitive nanorods protruding from one side of said electrode film opposite to said substrate, covering entirely said sensing region of said electrode film, and exhibiting an ion selectivity of absorbing an ion of interest thereon for inducing a surface potential corresponding to concentration of the ion of interest in the solution; and
    an encapsulant of an insulator enclosing said conductive base structure except for said sensing region of said electrode film and formed with a window for exposing said ion-sensitive nanorods to the solution;
    wherein each of said ion-sensitive nanorods has a conductive core made from an electrically conductive material and protruding from said electrode film, and an ion-sensitive layer formed on and enclosing said conductive core and made from an ion-sensitive material different from said electrically conductive material, said ion-sensitive material exhibiting the ion selectivity,
    wherein said ion-sensitive material is selected from titanium dioxide, tin dioxide, zinc oxide, ruthenium oxide, and iridium oxide.

11. The ion sensor of claim 10, wherein said conductive core of each of said ion-sensitive nanorods has a diameter ranging from 10-50 nm.

12. The ion sensor of claim 10, wherein said ion-sensitive layer of each of said ion-sensitive nanorods has a layer thickness ranging from 10-90 nm.

13. The ion sensor of claim 10, wherein said electrode film is made from said electrically conductive material.

14. The ion sensor of claim 10, wherein said electrically conductive material is indium tin oxide, tin oxide, or indium oxide.

15. The ion sensor of claim 14, wherein said electrically conductive material is indium tin oxide.

16. The ion sensor of claim 10, wherein said ion-sensitive material is titanium dioxide.

17. The ion sensor of claim 10, wherein said insulator of said encapsulant is made from epoxy resin.

18. The ion sensor of claim 10, wherein said substrate is made from glass.

* * * * *